United States Patent
Flohr et al.

(10) Patent No.: US 10,210,632 B2
(45) Date of Patent: Feb. 19, 2019

(54) STRUCTURE-COMPLIANT NOISE REDUCTION DURING MULTISPECTRAL COMPUTED TOMOGRAPHY IMAGING

(71) Applicants: Thomas Flohr, Uehlfeld (DE); Steffen Kappler, Effeltrich (DE); Rainer Raupach, Heroldsbach (DE); Harald Schöndube, Erlangen (DE)

(72) Inventors: Thomas Flohr, Uehlfeld (DE); Steffen Kappler, Effeltrich (DE); Rainer Raupach, Heroldsbach (DE); Harald Schöndube, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 132 days.

(21) Appl. No.: 15/091,658

(22) Filed: Apr. 6, 2016

(65) Prior Publication Data

US 2016/0300368 A1 Oct. 13, 2016

(30) Foreign Application Priority Data

Apr. 7, 2015 (DE) .......... 10 2015 206 127

(51) Int. Cl.
*G06F 19/00* (2018.01)
*G06T 11/00* (2006.01)

(52) U.S. Cl.
CPC ............ *G06T 11/005* (2013.01); *G06F 19/00* (2013.01); *G06F 19/321* (2013.01);
(Continued)

(58) Field of Classification Search
CPC ................ G06T 11/005; G06T 11/006; G06T 2211/421; G06T 2211/424
See application file for complete search history.

(56) References Cited

U.S. PATENT DOCUMENTS 6,529,575 B1 * 3/2003 Hsieh ............... G06T 5/002
378/4
8,233,586 B1 * 7/2012 Boas ............... G06T 5/002
378/207
(Continued)

FOREIGN PATENT DOCUMENTS

DE 102010043975 A1 5/2012
WO WO2012009725 A1 1/2012

OTHER PUBLICATIONS

Jeffrey F. Williamson et al., "On two-parameter models of photon cross sections: Application to dual-energy CT imaging," Med. Phys., vol. 33 (No. 11), pp. 4115-4129, (2006).
(Continued)

*Primary Examiner* — Gandhi Thirugnanam
(74) *Attorney, Agent, or Firm* — Lempia Summerfield Katz LLC

(57) ABSTRACT

A method for reconstructing image data during CT imaging is described. In the method, a plurality of independent data records of projection measured data are captured. A combined data record is then determined based on the captured data records. In addition, morphological information is determined based on the combined data record. A target data record is also determined based on the captured independent data records. A target image data record is reconstructed based on the target data record and the determined morphological information. An image data determination facility and a computed tomography system are also described.

16 Claims, 4 Drawing Sheets

(52) U.S. Cl.
CPC ....... *G06T 11/006* (2013.01); *G06T 2211/421* (2013.01); *G06T 2211/424* (2013.01)

(56) References Cited

U.S. PATENT DOCUMENTS

| | | | |
|---|---|---|---|
| 2003/0076988 A1* | 4/2003 | Liang | G06T 5/10 382/131 |
| 2006/0109949 A1* | 5/2006 | Tkaczyk | A61B 6/032 378/4 |
| 2008/0069294 A1* | 3/2008 | Wigstrom | A61B 6/032 378/4 |
| 2008/0226017 A1* | 9/2008 | Altman | A61B 6/482 378/4 |
| 2011/0293159 A1* | 12/2011 | Bruder | A61B 6/032 382/131 |
| 2011/0293160 A1* | 12/2011 | Bruder | A61B 6/032 382/131 |
| 2012/0121148 A1* | 5/2012 | Bruder | A61B 6/5211 382/131 |
| 2013/0108013 A1* | 5/2013 | Leng | A61B 6/032 378/19 |
| 2013/0259342 A1* | 10/2013 | Bruder | G06T 11/006 382/131 |
| 2016/0300368 A1* | 10/2016 | Flohr | G06T 11/005 |

OTHER PUBLICATIONS

Wonseok Huh et al., "Iterative Image Reconstruction for Dual-Energy X-Ray CT Using Regularized Material Sinogram Estimates," IEEE, pp. 1512-1515, (2011).

German Office Action for related German Application No. 10 2015 206 127.2 dated Dec. 22, 2015.

Yu Lifeng et al: "Dual-Energy CT-Based Monochromatic Imaging"; American Journal of Roentenology Nov. 2012; 199. Jg.; pp. 9-15; 2012.

* cited by examiner

STRUCTURE-COMPLIANT NOISE REDUCTION DURING MULTISPECTRAL COMPUTED TOMOGRAPHY IMAGING

CROSS-REFERENCE TO RELATED APPLICATIONS

The present patent document claims the benefit of DE 102015206127.2, filed on Apr. 7, 2015, which is hereby incorporated by reference in its entirety.

BACKGROUND

The present embodiments relate to a method for reconstructing image data during CT imaging. Furthermore, the embodiments relate to an image data determination facility. Moreover, the embodiments also relate to a computed tomography (CT) system.

With the help of modern imaging methods, two- or three-dimensional image data is frequently generated that may be used to visualize a mapped examination object and furthermore also for further applications.

The imaging methods are frequently based on the capture of x-ray radiation, wherein what is known as projection measured data is generated. Projection measured data may be acquired for instance with the aid of a CT system. With CT systems, an assembly disposed on a gantry (i.e., an x-ray source and an x-ray detector arranged opposite thereto) may circulate around a measuring space, in that the examination object (that, without loss of generality, is referred to below as the patient) is located. The center of rotation (also referred as 'isocenter') coincides here with what is known as a system axis z. In one or a number of circulations, the patient is irradiated with x-ray radiation from the x-ray source, wherein projection measured data or x-ray projection data is captured with the aid of the opposing x-ray detector.

The projection measured data generated, also abbreviated to projection data, is in particular dependent on the model design of the x-ray detector. X-ray detectors may have a plurality of detection units that are in most cases arranged in the form of a regular pixel array. The detection units each generate a detection signal for x-ray radiation striking the detection units, said detection signal being analyzed at specific time instants in respect of intensity and spectral distribution of the x-ray radiation, in order to obtain information on the examination object and to generate projection measured data.

With a series of applications of CT systems, a number of data records or projection data records of independent measurements that relate to the same object are captured. By way of example, the different data records may relate to the same object at different time instants. The different data records may also include image recordings of the object with different recording parameters, such as different spectral parts for example. Such data records are recorded for instance while using recordings having a number of energy thresholds, known as multi-energy scans. With multi-energy scans, data of a quanta-counting detector having one or a number of energy thresholds is captured, wherein different data records are assigned to the respective energy ranges that are separated from the energy thresholds.

With the aforementioned quanta-counting or photon-counting x-ray detectors, the detection signal for x-ray radiation is analyzed in respect of intensity and spectral distribution of the x-ray radiation in the form of count rates. The count rates are made available as output data of what is known as a detector channel, which is assigned to a detection unit in each case. With quanta- or photon-counting detectors having a number of energy thresholds, each detector in most cases generates a set of count rates per projection on the basis of the respective detection signal of the detection unit. With the aid of the set of count rates, data records may be generated for a number of different energy threshold values that are in particular checked at the same time.

The individual different data records have a poorer quanta statistic, i.e. an increased statistical noise, than if the data records were available as a sum. This is then particularly the case if in the case of two energy thresholds, these energy thresholds are arranged closely around the energy value of the K-edge of a material that is used to map this material selectively. A similar problem occurs if, instead of spectrally separated individual images, base material images are to be reconstructed.

The problem overall then is that the statistical quality of the individual data records is significantly poorer than that of the overall data record that results in individual images with artifacts due to noise effects.

One possibility of improving the image quality of the individual images is in using all data records together during the reconstruction of image data, but on this basis, to reconstruct a spectral image or a base material image, wherein the time instant is defined by the system matrix, i.e. by the modeling of the measurement process of the selected spectral component or of the material component. Such an approach is described for instance in W. Huh and J A. Fessler, "Iterative image reconstruction for dual-energy x-ray CT using regularized material sinogram estimates", IEEE (2011), 1512-1515. Attempts are made here to use the statistics generically, i.e. by statistical weighting of the input data. In respect of a precise reproduction of the structures to be mapped, such an approach is ineffective since the approach entails a strong smoothing, i.e. reduction in the spatial resolution. In other words, the morphological information gets lost during the reconstruction of the individual images. Moreover, due to the complexity of the system matrix and its iterative application, such methods require a very high computing outlay.

With another conventional method, a data record with good statistics is used in a spatial frequency-selective manner as a priori information and a spectral or material component is thus optimized. Although a reconstruction method based on this approach is significantly faster than with the approach described above, this method is similarly disadvantageous in that the method fails to obtain morphological information when the individual images are being reconstructed. The morphological information is only retained here for instance with low spatial frequencies, in other words larger object structures, and gets lost with high spatial frequencies. With both conventional approaches, filtering takes place in the reconstruction act without taking into account the structural information.

SUMMARY AND DESCRIPTION

It is thus an object of the present embodiments, during imaging based on independent projection data records of the same object, to enable a mapping with noise reduction and an improved reproduction of the structures to be mapped.

With a method for reconstructing image data during CT imaging, a number of independent data records of projection measured data are captured. A combined data record is determined based on the captured data records. This combined data record includes a combination of the captured data records. For example, a combination may be a sum of the captured data records. The combination of captured data records is selected such that the combination is noise-reduced in relation to the individual captured data records. A simple sum of all captured data records is already significantly noise-reduced in comparison with the individual data records. Alternatively, a weighted sum may also be used for further noise reduction.

Furthermore, morphological information based on the combined data record is determined with the method. Morphological information is information relating to the structures of an object to be mapped.

This morphological information is contained both in the individual captured data records and in the combination of the captured data records. Because the combined data record has a better statistical quality, the structures may be determined more reliably and more precisely based on the combined data record. In addition, one or a number of target data records is/are also determined based on the captured independent data records. An individual target data record may have one of the individual captured data records of the projection measured data. However, an individual target data record may also include a base material decomposition from the captured data records, or may be the result of a more complex processing of the individual data records (e.g., a virtual native image). Such a base material decomposition is described in J F Williamson, et al., "On two-parameter models of photon cross sections: Application to dual-energy CT imaging," Med. Phys. 33 (2006), 4115-4129. A target data record includes the projection measured data that forms the basis of an individual image or a target image to be reconstructed. Target data records are subjected to a stronger noise than the combined data record already described.

In order to achieve an improved structural integrity at the same time as an improved statistical quality of the target images, the target images are determined by reconstruction based on the target data records and by taking the determined morphological information into account. Taking the structural information of the combined data record into account during the reconstruction achieves an improved structural integrity of the reconstructed images. In the context of CT imaging, the term reconstruction is to be understood as the reconstruction of image data from projection measured data, and a filtered back projection may be included within the scope of the reconstruction.

The image data determination facility for reconstructing image data during CT imaging has an input interface for capturing a number of independent data records of projection measured data. The image data determination facility also includes a data record determination unit for determining a combined data record based on the captured data records. Part of the image data determination facility is a structural information determination unit for determining morphological information based on the combined data record. Moreover, the image data determination facility also has a filter determination unit for determining a locally adaptive filter based on the morphological information. In addition, the image data determination facility includes a target data record determination unit for determining a target data record based on the captured data records and a reconstruction unit for reconstructing a target image data record based on the target data record by using the locally adaptive filter. The reconstruction unit performs the functions of a typical reconstruction unit of a CT system. Furthermore, the reconstruction unit has the additional function that during the reconstruction the reconstruction unit takes the locally adaptive filter determined by the filter determination unit into account. Alternatively, the locally adaptive filter may be applied to the target image data records after the actual reconstruction.

The computed tomography system has the image data determination facility.

The principal components of the image data determination facility may be provided mainly in the form of software components. In particular, the data record determination unit, the structural information determination unit, the filter determination unit, the target data record determination unit and the reconstruction unit may be software components. These software components may be provided to some extent (e.g., if particularly rapid calculations are involved) by of software-assisted hardware (e.g., FPGAs, etc.). Similarly, if data is only being taken over from other software components, the interfaces may be provided as software interfaces. The interfaces may be provided as interfaces constructed using hardware, controlled by suitable software.

In particular, the image data determination facility may be part of a user terminal or a control facility of a CT system.

A largely software-based implementation may be provided in control facilities currently already in use, and may be easily retrofitted by a software update to operate in the desired manner. In this respect, the object is also achieved by a corresponding computer program product having a computer program. The computer program may be loaded directly into a memory of a control facility of a computed tomography system, having program sections, to perform all acts of the method, if the program is executed in the control facility. Such a computer program product may, in addition to the computer program, include additional components, such as documentation and/or additional components, as well as hardware components, such as hardware keys (e.g., dongles etc.) for use of the software.

A computer-readable medium (e.g., a memory stick, a hard disk or another transportable or fixedly integrated data carrier) upon which the program sections of the computer program may be read in and executed by a computing unit of the control facility, may be used for transportation to the control facility and/or for storage on or in the control facility. The computing unit may include one or a plurality of interoperating microprocessors or the like.

The dependent claims and the description that follows each contain particularly advantageous embodiments and developments. Here, the claims of a claim category can in particular also be developed analogously to the dependent claims of another claim category. Moreover, the various features of different exemplary embodiments and claims can also be combined to form new exemplary embodiments.

In one embodiment of the method, the morphological information is used during the reconstruction act of the target image data record to the effect that a filter is provided based on the morphological information, said filter being used during the reconstruction (e.g., by filtered back projection). The filter is preferably provided asymmetrically as a function of the determined morphology.

In a further embodiment of the method, the morphological information is used during the reconstruction act of the target image data record to the effect that a filter is designed based on the morphological information, said filter being used to perform a filtering of the target image data records following the reconstruction. The filter may be provided asymmetrically as a function of the determined morphology.

In a preferred embodiment of the method, the independent data records of projection measured data include data records with different recording parameters. Alternatively or in addition, the independent data records of projection measured data include data records that are assigned to different recording time instants.

The different recording parameters may include different x-ray spectra or spectral distributions. For instance, projection measured data records are captured with detectors having a number of energy thresholds, said projection measured data records being assigned to different energy sections of the x-ray spectrum. The projection measured data assigned to individual spectral parts may also be obtained by an image recording with the aid of a dual-source CT system. Projection measured data with different x-ray spectra is captured here with a plurality of detectors arranged at different positions, said x-ray spectra being generated by different x-ray sources. The projection measured data assigned to the individual spectral parts may also be captured within the by an image recording with the aid of another CT system that is configured to record spectral data (e.g., a CT device with a rapid periodic change in the x-ray voltage during the CT scan), a CT device with different spectral prefiltering of the quanta emitted by the x-ray tube, or a CT device with dual-layer or multi-layer detectors.

In an embodiment of the method, the combined data record is determined as a noise variance-dependent weighted sum of the independent data records of projection measured data. The noise variance may be determined as an average image noise in the individual images (e.g., measured as a standard deviation in the pixel values in the area to be mapped). The noise variance may also be defined as image noise in certain subareas of particular interest in the area to be mapped or alternatively as average noise of the projection measured data that is used to calculate the image data.

In an alternative embodiment of the method, the combined data record includes a number of differently optimized data records with differently weighted sums. A plurality of separately optimized data records may be assigned to different materials with different spectral properties, such that with one optimized data record, the signal-to-noise ratio is optimized for a first material, and with another optimized data record, the signal-to-noise ratio is optimized for a second material. A sum is understood in this context to be a sum of captured data records of projection measured data that, depending on the assigned material, has different weighting factors.

As discussed above, different materials may be assigned to the differently optimized data records.

Combined image data record is reconstructed in the act of determining morphological information and structural information describing the strength and direction of contrast edges is obtained with the aid of edge-selective filters. To obtain structural information, image data is obtained based on the noise-optimized combined projection measured data record. Contrast edges are then determined in the determined image data with the aid of edge-selective filters. Such a filtering is described for instance in DE 10 2010 043 975 A1.

In one embodiment of the method, in which a number of differently optimized data records are determined, structural information is obtained based on the individual, differently optimized data records and the data records are then combined to form overall structural information. This may be provided to obtain the overall structural information, the maximum strength of the two individual pieces of information and the direction associated with the corresponding material are used in each case.

The maximum strength of the individual structural information (e.g., the strength of the locally more pronounced contrast edge of both items of structural information) and the direction associated with the corresponding material with the locally more pronounced contrast edge are taken into account for the overall structural information. A clearly outlined mapping may be achieved during the reconstruction of the target image.

In order to take the morphological information into account during the reconstruction of the target image data record, a locally adaptive filter is determined based on the morphological information. In one reconstruction act of the target image data record, the morphological information is used as a filter as a filtered back projection. Alternatively, a locally adaptive filter may be determined such that, during an iterative reconstruction, is used as a regularization term for instance. Alternatively, a locally adaptive filter may be determined such that, after the reconstruction, is applied to the target image data records.

In an embodiment of the method, the locally adaptive filter is provided as a bilateral filter, the domain filter of which is locally asymmetrically pronounced such that the filter length parallel to the respective contrast edge in the combined image data record is longer than that at right angles to the contrast edge. The ratio between the filter axes may correspond approximately to the edge strength. For example, the filter may be isotropic in the event that no contrast edges are detected. The cited contrast edges are understood to mean intensity differences in the image or discontinuities in the attenuation values.

During the act of reconstructing the target image data record, an iterative reconstruction may be applied to reconstruct the target image data record, the regularization strength of which is locally dependent on the determined morphological information. A regularization strength is to be understood as a locally varying variable that is used to determine the degree of local smoothing in the target image.

In an alternative embodiment of the method, one of the independent data records, or one data record that was obtained by a base material decomposition of the number of independent data records, is selected as the target data record.

Alternatively, during dynamic imaging, a projection data record assigned to a certain time instant of the projection data recording is selected as a target data record, and the average of all captured projection data records over time is determined as the combined data record.

DETAILED DESCRIPTION

Figure 1:
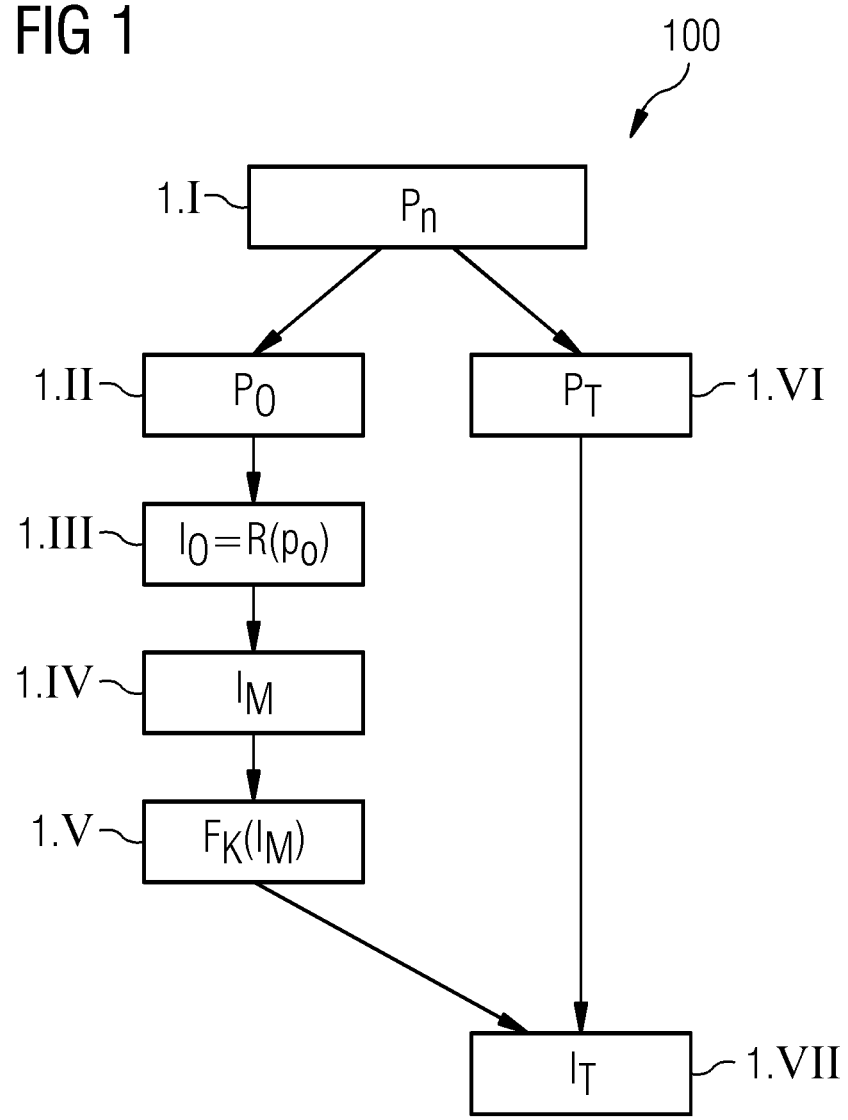
FIG. 1 shows a flow diagram that illustrates a method for reconstructing image data during CT imaging according to an exemplary embodiment.

FIG. 1 illustrates a method 100 for reconstructing image data during CT imaging of an object O to be examined (see FIG. 4) according to an exemplary embodiment. In act 1.I of the method 100, a number of N spectral projection data records Pn are captured. To this end, acquisition control signals are transmitted to a measuring unit of a CT system 1 (e.g., FIG. 4). In this described exemplary embodiment, N different projection data records $P_n$ with a different frequency spectrum are recorded. The different frequency spectra may result from the detection of the x-ray radiation using detectors having a number of energy thresholds.

In act 1.II, an optimized data record $P_0$ is calculated, that, in comparison to a target data record $P_T$ to be calculated later, has an improved quanta usage. This improved quanta usage is achieved by the optimized data record $P_0$ calculated from a noise variance-dependent weighted sum, using equation 1:

$$P_0 = \sum_n \frac{1}{\sigma^2} P_n. \quad (1)$$

In equation 1, $\sigma$ represents the noise variance of the measured data record $P_n$. The noise variance may be considered to be a measure of the image noise in an individual measured data record $P_n$.

In act 1.III, an optimized image data record is reconstructed, according to equation 2:

$$I_0 = R(P_0) \quad (2)$$

In equation 2, R may be a filtered back projection. In act 1.IV, structural information $I_M$ is obtained with the aid of edge-selective filters. The edge-selective filters describe the strength and direction of the contrast edges occurring in the optimized image data record $I_0$. Filters of this type are described in DE 10 2010 043 975 A1.

In act 1. V, a locally adaptive filter $F_K(I_M)$ is determined based on the contrast edges determined in act 1.IV. The locally adaptive filter have a stronger filter effect parallel to the determined contrast edges than at right angles thereto. In other words, the filter length parallel to the contrast edges is greater than at right angles to the edges. The ratio between the axes of the filter may correspond approximately to the edge strength of the contrast edges in $I_0$.

In act 1.VI, one or a plurality of target data records $P_T$ is/are determined based on the captured N spectral projection data records $P_n$, that, in the exemplary embodiment shown in FIG. 1, each include one of the data records $P_n$. In this exemplary embodiment, the target data records $P_T$ correspond to the measured projection data records $P_n$.

In act 1.VII, an optimized image data record $I_T$ is determined in each case based on the target data records $P_T$ with the aid of a reconstruction R'. During the reconstruction R', a filtered back projection is performed using the locally adaptive filter $F_K(I_M)$ determined in act 1. V. This filter has the effect that a more pronounced filtering is performed parallel to the contrast edges determined in $I_0$ than at right angles to said contrast edges.

The target image data records $P_T$ are smoothed without blurring the contours. Structural information is therefore obtained from a noise-optimized sum image, said structural information being used during the generation of individual images for contour-preserving reconstruction.

Figure 2:
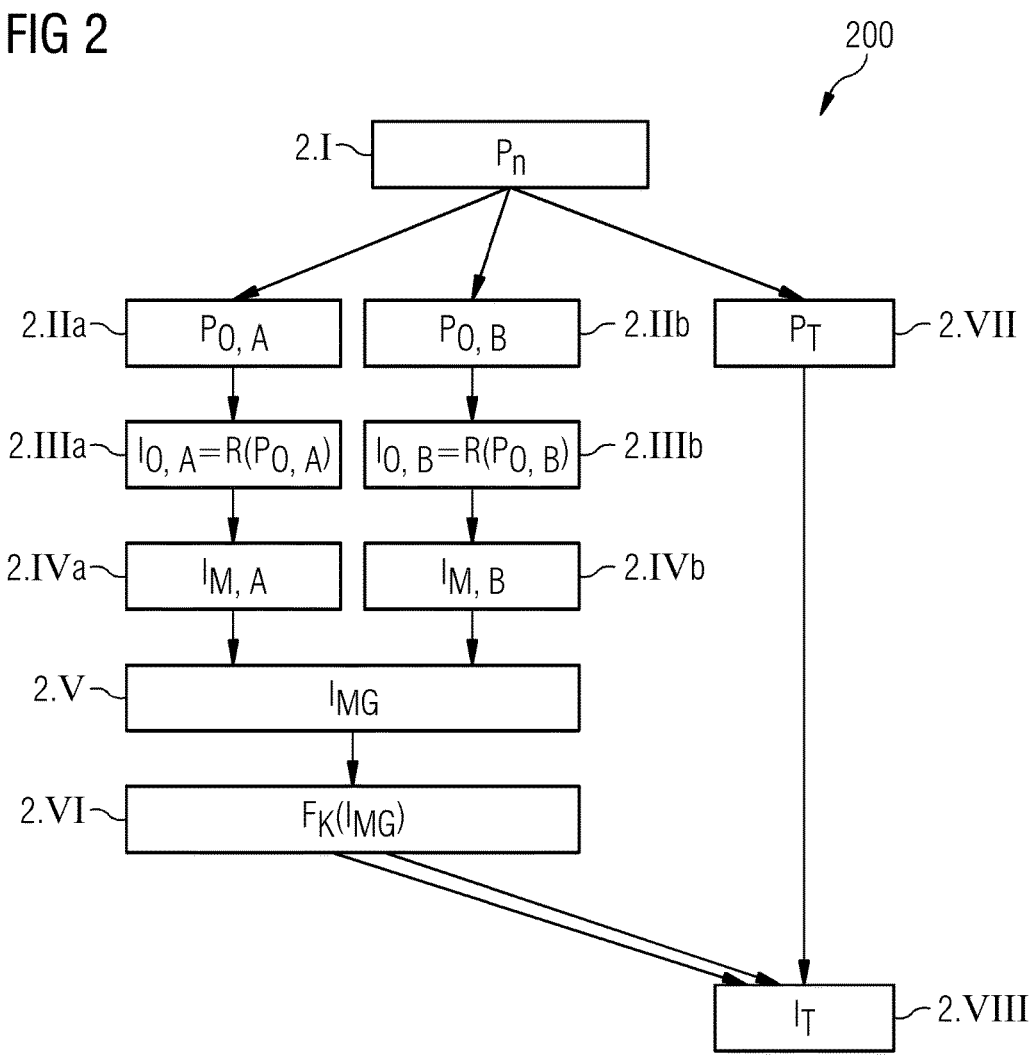
FIG. 2 shows a flow diagram that illustrates a method for reconstructing image data during CT imaging according to another exemplary embodiment.

FIG. 2 shows a method 200 for reconstructing image data during CT imaging according to another exemplary embodiment. It is taken into account in the method 200 that the object O to be mapped has different materials (e.g., A, B) with significantly different spectral properties.

A plurality of N spectral projection data records $P_n$ are captured in act 2.I, as in the method 100 in FIG. 1. Here part of the captured projection data records $P_{n,A}$ have projection data that is assigned to the material A, and part of the captured projection data records $P_{n,B}$ have projection data that is assigned to the material B.

A first optimized data record $P_{0,A}$ of the first material A, that only takes the projection data records $P_{n,A}$ assigned to the first material A into account, is then calculated in act 1.IIa. In comparison to a target data record $P_T$ to be calculated subsequently, this first data record has an improved quanta usage. This improved quanta usage is achieved in that the first optimized data record $P_{0,A}$ is calculated from a noise variance-dependent weighted sum of the projection data records $P_{n,A}$ assigned to this material. A sum of data records has a better quanta usage than individual images, such as those used for the target data record $P_T$.

In act 2.IIIa, a first optimized image data record $I_{0,A} = R(P_{0,A})$ is reconstructed, and R may be a filtered back projection. In act 2.IVa, structural information $I_{M,A}$ is then obtained with the aid of edge-selective filters.

Similarly to act 2.IIa, a second optimized data record $P_{0,B}$ of the material B is also calculated in act 2.IIb, only taking the projection data records $P_{n,B}$ assigned to the material into account. In comparison to a target data record $P_T$ to be calculated subsequently, this second data record has an improved quanta usage. This improved quanta usage is achieved in that the second optimized data record $P_{0,B}$ is calculated from a noise variance-dependent weighted sum of the projection data records $P_{n,B}$ assigned to this material B. As already mentioned, a sum of projection data records has an improved quanta usage compared with individual data records. In order to further improve the signal-to-noise ratio of the optimized data records, the summands of the optimized data records $P_{n,B}$ are weighted in a noise variance-dependent manner.

In act 2.IIIb, a second optimized image data record $I_{0,B} = R(P_{0,B})$ is reconstructed, wherein R may be a filtered back projection. In act 2.IVb, structural information $I_{M,B}$ is obtained with the aid of edge-selective filters.

In act 2.V, overall structural information $I_{MG}$ is obtained for the individual materials A, B based on the structural information $I_{M,A}$, $I_{M,B}$, with the maximum strength of the individual structural information $I_{M,A}$ and $I_{M,B}$. In other words, the strength of the contrast edge, that is more pronounced locally or at one position, of both pieces of structural information $I_{M,A}$, $I_{M,B}$ and the direction associated with the corresponding material A, N with the locally more pronounced contrast edge are taken into account for the overall structural information.

In act 2.VI, a locally adaptive filter $F_K(I_{MG})$ is determined based on the overall structural information $I_{MG}$ determined in act 2.V.

In act 2.VII, a plurality of target data records $P_T$ are determined based on the captured N spectral projection data records $P_n$, that, in the exemplary embodiment shown in FIG. 2, each include a spectral data record $P_n$. The target data records therefore correspond to the measured projection data records $P_n$.

In act 2.VIII, optimized image data records $I_T$ are reconstructed based on the target data records $P_T$, and during the reconstruction R' a filtered back projection is performed using the locally adaptive filter $F_K(I_M)$ determined in act 2.VI. The target image data records $I_T$ are smoothed without blurring the contours. Structural information is therefore obtained from a noise-optimized sum image, said structural information being used during the generation of individual images for contour-preserving reconstruction. Alternatively, after the filtered back projection, the locally adaptive filter $F_K(I_{MG})$ may be used in the image space in order to obtain the target data records.

Figure 3:
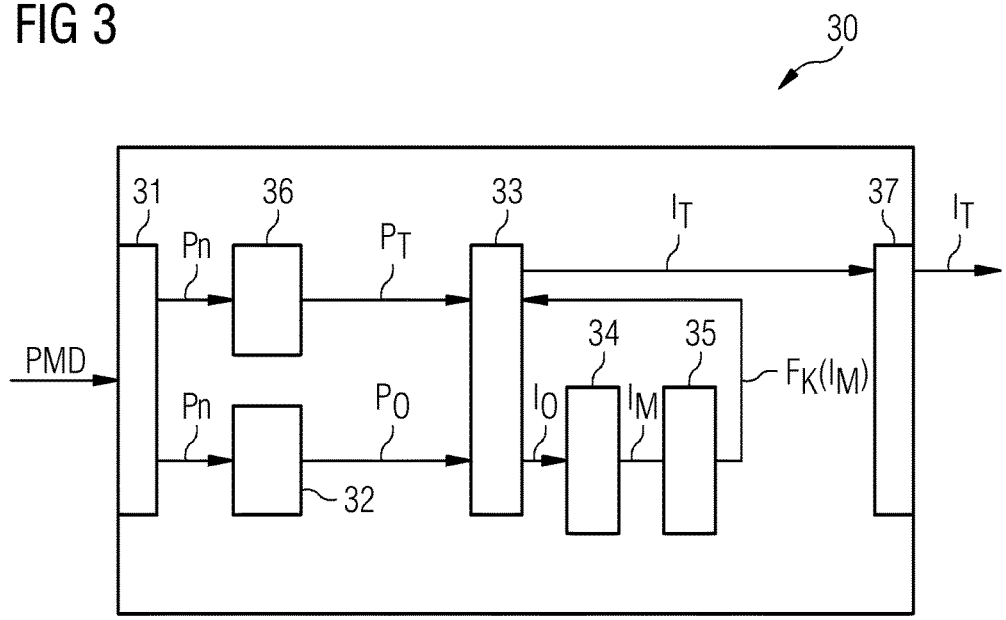
FIG. 3 shows a block diagram with an image data determination facility according to an exemplary embodiment.
Figure 4:
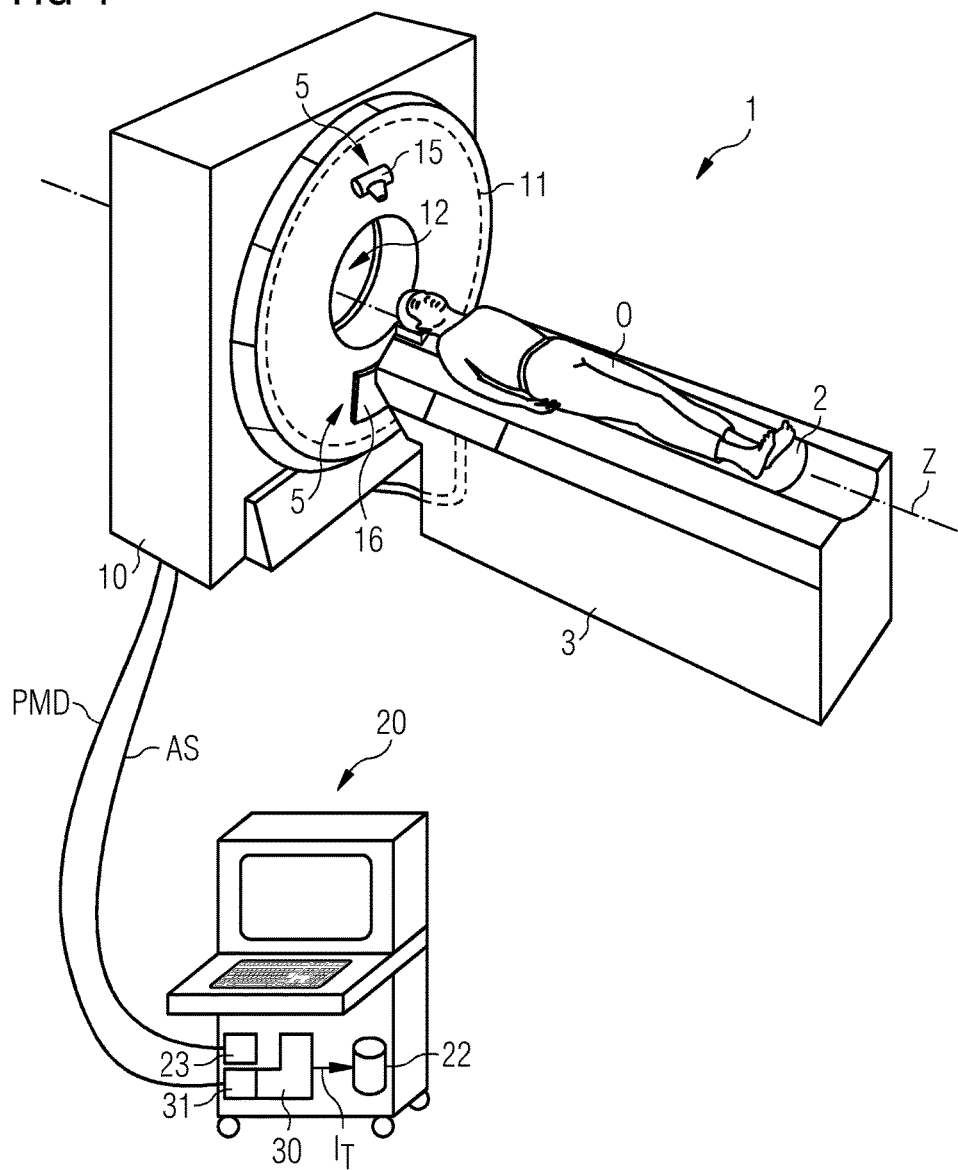
FIG. 4 shows a schematic representation of a computed tomography system according to another exemplary embodiment.

FIG. 3 shows an image data determination facility 30 according to an exemplary embodiment. For example, the image data determination facility 30 may be part of a control facility 20 of a CT system 1 (e.g., as shown in FIG. 4). The image data determination facility 30 includes an input interface 31 that receives projection data PMD from a measuring facility (e.g., FIG. 4) of a CT system 1. The projection data PMD may include projection data records $P_n$, with each of the projection data records $P_n$ recorded independently. The individual projection data records $P_n$ are recorded with detectors having a number of energy thresholds or having various detectors at various positions.

A data record determination unit 32, that is part of the image data determination facility 30, receives projection data records $P_n$ from the input interface 31 and determines a combined data record $P_0$ based on the received data records $P_n$. The combined data record $P_0$ is transmitted to a reconstruction unit 33 that reconstructs noise-optimized image data $I_0$ based on the received combined data record $P_0$. The reconstruction is performed with the aid of a filtered back projection, and the filter may be isotropic. The noise-optimized image data $I_0$ is transmitted to a structural information determination unit 34 that determines morphological information $I_M$ based on noise-optimized image data $I_0$. The morphological information $I_M$ includes information relating to the strength and orientation of contrast edges for instance. The determined morphological information $I_M$ is then transmitted to a filter determination unit 35. The filter determination unit 35 determines a locally adaptive filter $F_K(I_M)$ based on the morphological information $I_M$.

Furthermore, the image data determination facility 30 includes a target data record determination unit 36. The target data record determination unit 36 receives projection data records $P_n$ from the input interface 31 and determines at least one target data record $P_T$ based on the received data records. The target data record $P_T$ is transmitted to the reconstruction unit 33 that also receives data from the filter determination unit 35 relating to the determined locally adaptive filter $F_K(I_M)$. The reconstruction unit 33 reconstructs a target image data record $I_T$ using the locally adaptive filter $F_K(I_M)$ based on the target data record $P_T$. A number of target data records $P_T$ may also be determined based on the captured projection data, and a plurality of target image data records $I_T$ may be obtained. The target image data $I_T$ is transferred to an output interface 37. The output interface 37 outputs the target image data $I_T$ to other units (e.g., a storage unit or a graphic display unit, such as a terminal or a monitor).

A computed tomography system (CT system) 1 with an image data determination facility 30 according to an exemplary embodiment is shown schematically in FIG. 4.

The CT system 1 includes a scanner 10 and, a gantry 11, with a projection data acquisition unit 5 having a detector 16 and an x-ray source 15 opposing the detector 16 that circulates about a measuring space 12. A patient support facility 3 or a patient couch 3, and the upper part 2 with a patient O resting thereupon may be moved toward the scanner 10, is located in front of the scanner 10 in order to move the patient O through the measuring space 12 relative to the detector system 16. The scanner 10 and the patient couch 3 are controlled by a control facility 20, from which acquisition control signals AS originate from a conventional control interface 23, in order to control the entire system in a conventional manner in accordance with predetermined measurement protocols P. Through the motion of the patient O along the z-direction, corresponding to the system axis z lengthways through the measuring space 12, and the simultaneous circulation of the x-ray source 15, a helical path is produced for the x-ray source 15 relative to the patient O during the measurement. The detector 16 runs in parallel opposite the x-ray source 15 to capture projection measured data PMD that is used to reconstruct volume and/or layer image data.

A sequential measuring method may also be performed, in which a fixed position is approached in the z-direction and the projection measured data PMD is then captured during a circulation, a partial circulation or a number of circulations at the relevant z-position to reconstruct a cross-sectional image at this z-position or to reconstruct volume image data from the projection data of a number of z-positions.

The method may also be used on other CT systems (e.g., with a number of x-ray sources and/or detectors, and/or with a detector forming a complete ring).

The projection measured data PMD acquired by the detector 16 (e.g., raw data) is transferred to the control facility 20, or the image data determination facility 30 contained therein, via a raw data interface that is the input interface 31 of the image data determination facility 30. This raw data is processed by the image data determination facility 30 in the afore-described manner. In this exemplary embodiment, the image data determination facility is provided in the control facility 20 in the form of software on a processor.

After the processing by the image data determination facility 30, the low-noise image data $I_T$ determined by the image data determination unit is output to a storage unit 22 and/or to an output unit of the control facility 20 of the CT system.

Finally, it may again be noted that the methods and apparatuses described above are merely preferred exemplary embodiments and may be varied by a person skilled in the art without departing from the scope of the as defined by the claims. The method and the image data determination facility are primarily described based on the processing of spectrally different projection data. However, various embodiments may also be applied to the low-noise image data reconstruction of projection data records recorded at different time instants. The various embodiments are not restricted to an application in the medical field and may be applied to the recording of CT images for other purposes (e.g., for material testing, etc.). Likewise, the term "unit" may refer to a number of components, and the components may be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for reconstructing image data during CT imaging, the method comprising:

capturing a plurality of independent data records of projection measurement data;

determining a combined data record based on the captured independent data records, wherein the combined data record comprises a plurality of differently optimized data records with differently weighted sums;

determining morphological information based on the combined data record;

determining a target data record based on the captured independent data records; and reconstructing a target image data record based on the target data record and the determined morphological information.

2. The method of claim 1, wherein the independent data records of the projection measured data comprise data records with different recording parameters, different recording time instants, or different recording parameters and different recording time instants.

3. The method of claim 2, wherein the different recording parameters comprise different x-ray spectra or spectral distributions.

4. The method of claim 1, wherein the differently weighted sums are weighted in a noise variance-dependent manner.

5. The method of claim 1, wherein the differently optimized data records are assigned different materials, the differently optimized data records represent a combination of data records assigned to different materials, or the differently optimized data records emerge from the target data record due to removal of data records assigned to certain materials.

6. The method claim 1, wherein the determining of the morphological information comprises reconstructing a combined image data record and obtaining structural information with aid of edge-selective filters, the structural information describing a strength and a direction of contrast edges.

7. The method of claim 1, wherein overall structural information is obtained by determining a plurality of differently optimized data records based on individual, differently optimized data records and combining the plurality of differently optimized data records to form the overall structural information.

8. The method of claim 1, wherein a locally adaptive filter is determined based on the morphological information, and wherein the reconstruction of the target image data record includes filtered back projection, wherein the locally adaptive filter is used as a filter, a locally adaptive filter, or a filter and a locally adaptive filter, the filter being used as a filter after the reconstruction of the target image data record in the image space, the locally adaptive filter based on the morphological information, the filter being used as a filter in reconstruction act of the target image data record via iterative reconstruction.

9. The method claim 8, wherein the locally adaptive filter comprises a bilateral filter, wherein a domain filter of the locally adaptive filter is locally asymmetrically pronounced such that a filter length parallel to a contrast edge is longer than at right angles to the contrast edge.

10. The method of claim 9, wherein the iterative reconstruction is used to reconstruct the target image data record, wherein a regularization strength of the iterative reconstruction is locally dependent on the determined morphological information.

11. The method claim 10, wherein as a target data record, one of the independent data records is selected or one of the independent data records that was obtained by a base material decomposition of the plurality of independent data records is selected, or a projection data record assigned to a time instant of the projection data recording is selected and an average of all captured projection data records over time is determined as a combined data record.

12. An image data determination facility for reconstructing image data during CT imaging, the facility comprising:

an input interface configured to capture a plurality of independent data records of projection measured data;

a data record determination unit configured to determine a combined data record based the captured independent data records;

a structural information determination unit configured to determine morphological information based on the combined data record;

a filter determination unit configured to determine a locally adaptive filter based on the morphological information;

a target data record determination unit configured to determine a target data record based on the captured independent data records; and a reconstruction unit configured to reconstruct a target image data record based on the target data record using the locally adaptive filter, wherein the reconstruction of the target image data record comprises a filtered back projection, wherein the locally adaptive filter is configured to be used as a filter, a locally adaptive filter, or a filter and a locally adaptive filter, wherein the filter is configured to be used as a filter in the reconstruction of the target image data record via iterative reconstruction, wherein the filter is configured to be used as a filter after the reconstruction of the target image data record in the image space, wherein the locally adaptive filter comprises a bilateral filter, and wherein a domain filter of the locally adaptive filter is locally asymmetrically pronounced such that a filter length parallel to a contrast edge is longer than at right angles to the contrast edge.

13. A computed tomography system comprising:

a control facility with an image data determination facility, wherein the image data determination facility comprises:

an input interface for capturing a plurality of independent data records of projection measured data;

a data record determination unit for determining a combined data record based the captured independent data records, wherein the combined data record comprises a plurality of differently optimized data records with differently weighted sums;

a structural information determination unit for determining morphological information based on the combined data record;

a filter determination unit for determining a locally adaptive filter based on the morphological information;

a target data record determination unit for determining a target data record based on the captured independent data records; and a reconstruction unit for reconstructing a target image data record based on the target data record using the locally adaptive filter.

14. A non-transitory computer-readable medium with stored program sections configured to be read in and executed by a computing unit, and when executed are configured to:
- capture a plurality of independent data records of projection measurement data;
- determine a combined data record based on the captured independent data records;
- determine morphological information based on the combined data record comprising reconstructing the combined image data record and obtaining structural information with the aid of edge-selective filters, wherein the structural information describes the strength and direction of contrast edges, and wherein the structural information is obtained by determining a plurality of differently optimized data records based on individual, differently optimized data records and combining the plurality of differently optimized data records to form the structural information;
- determine a target data record based on the captured independent data records; and
- reconstruct a target image data record based on the target data record and the determined morphological information.

15. The method of claim 14, wherein a locally adaptive filter is determined based on the morphological information, and wherein the reconstruction of the target image data record includes filtered back projection, wherein the locally adaptive filter is used as a filter, a locally adaptive filter, or a filter and a locally adaptive filter, the filter being used as a filter after the reconstruction of the target image data record in the image space, a locally adaptive filter based on the morphological information, the filter being used as a filter in reconstruction act of the target image data record via iterative reconstruction.

16. The method claim 15, wherein the locally adaptive filter comprises a bilateral filter, wherein a domain filter of the locally adaptive filter is locally asymmetrically pronounced such that a filter length parallel to a contrast edge is longer than at right angles to the contrast edge.

* * * * *